United States Patent
Eun et al.

(10) Patent No.: US 11,441,175 B2
(45) Date of Patent: Sep. 13, 2022

(54) METHODS AND KITS FOR DEPLETING UNDESIRED NUCLEIC ACIDS

(71) Applicant: BIOO Scientific Corporation, Austin, TX (US)

(72) Inventors: Suk Ho Eun, Austin, TX (US); Adam Morris, Red Rock, TX (US)

(73) Assignee: BIOO Scientific Corporation, Austin, TX (US)

( * ) Notice: Subject to any disclaimer, the term of this patent is extended or adjusted under 35 U.S.C. 154(b) by 165 days.

(21) Appl. No.: 15/905,952

(22) Filed: Feb. 27, 2018

(65) Prior Publication Data

US 2018/0258477 A1   Sep. 13, 2018

Related U.S. Application Data

(60) Provisional application No. 62/464,321, filed on Feb. 27, 2017.

(51) Int. Cl.
| | |
|---|---|
| *C12Q 1/6848* | (2018.01) |
| *C12Q 1/6806* | (2018.01) |
| *C12Q 1/6832* | (2018.01) |
| *C12Q 1/6855* | (2018.01) |
| *C12Q 1/686* | (2018.01) |
| *C12Q 1/6874* | (2018.01) |
| *C12Q 1/6888* | (2018.01) |
| *C12Q 1/6811* | (2018.01) |

(52) U.S. Cl.
CPC ......... *C12Q 1/6848* (2013.01); *C12Q 1/6806* (2013.01); *C12Q 1/686* (2013.01); *C12Q 1/6811* (2013.01); *C12Q 1/6832* (2013.01); *C12Q 1/6855* (2013.01); *C12Q 1/6874* (2013.01); *C12Q 1/6888* (2013.01); *C12Q 2600/16* (2013.01)

(58) Field of Classification Search
CPC .. C12Q 1/6848; C12Q 1/6874; C12Q 1/6806; C12Q 1/6888; C12Q 1/6832; C12Q 1/6855; C12Q 1/686; C12Q 1/6811; C12Q 2600/16
See application file for complete search history.

(56) References Cited

U.S. PATENT DOCUMENTS

| | | | | |
|---|---|---|---|---|
| 5,849,547 A * | 12/1998 | Cleuziat | ............... | C12Q 1/6844 435/91.21 |
| 7,932,034 B2 * | 4/2011 | Esfandyarpour | ..... | C12Q 1/6869 435/6.11 |
| 2005/0227257 A1 * | 10/2005 | Abravaya | ............ | C12Q 1/6832 435/6.11 |
| 2008/0312099 A1 * | 12/2008 | Wang | ................... | C12Q 1/6837 506/9 |
| 2012/0322691 A1 * | 12/2012 | Sachidanandam | ... | C12Q 1/6876 506/16 |
| 2015/0275267 A1 | 10/2015 | O'Neil et al. | | |
| 2016/0053304 A1 | 2/2016 | Wurtzel et al. | | |

FOREIGN PATENT DOCUMENTS

| | | | | |
|---|---|---|---|---|
| WO | WO-2012/033687 A1 | 3/2012 | | |
| WO | WO-2013/010062 A2 | 1/2013 | | |
| WO | WO-2016164866 A1 * | 10/2016 | ........... | C12Q 1/6848 |

OTHER PUBLICATIONS

Nichols et al. Current Protocols in Molecular Biology 2008; 3:15.1-3.15.4. (Year: 2008).*
Teer et al. Systematic comparison of three genomic enrichment methods for massively parallel DNA sequencing. Genome Research 2010; 20: 1420-1431 (Year: 2010).*
Gnirke et al. Solution hybrid selection with ultra-long oligonucleotides for massively parallel targeted sequencing. Nature Biotechnology 2009; 27: 182-189 (Year: 2009).*
Extended Search Report for European Application No. 18758015.4, dated Nov. 5, 2020.

* cited by examiner

*Primary Examiner* — Angela M. Bertagna
(74) *Attorney, Agent, or Firm* — Julie K. Staple; Dinsmore & Shohl LLP

(57) ABSTRACT

Methods and kits for depleting amplicons that correspond to undesired RNA species present in a sample are provided. The disclosed methods and kits employ a blocker that anneals with at least a portion of the undesired RNA, resulting in a duplex that is not a suitable substrate for ligating an adapter to the end of the undesired RNA.

40 Claims, 6 Drawing Sheets

Specification includes a Sequence Listing.

METHODS AND KITS FOR DEPLETING UNDESIRED NUCLEIC ACIDS

CROSS-REFERENCE TO RELATED APPLICATIONS

This application claims the benefit of U.S. Provisional Application Ser. No. 62/464,321 filed Feb. 27, 2017, which is incorporated by reference in its entirety.

SEQUENCE LISTING

The instant application contains a Sequence Listing which has been submitted electronically as an ASCII text file and is hereby incorporated by reference in its entirety. Said ASCII text file, created on Feb. 28, 2018, is named BIO027US_ST25.txt and is 802 bytes in size.

STATEMENT REGARDING FEDERALLY SPONSORED RESEARCH

This work was performed in part with Government support under National Science Foundation Award #1431020. The Government may have certain rights in the claimed inventions.

FIELD

The current teachings relate generally to the field of nucleic acid sequencing, particularly to sequencing DNA libraries generated from small RNA molecules and the amplified species present in such libraries. More particularly, the current teachings are directed to depleting certain undesired RNA species that are initially present in a sample so that the corresponding amplification products for such species are under-represented or lacking in sequencing libraries generated from the sample.

BACKGROUND

Small RNA sequencing using next generation sequencing technologies (sRNA-seq) is a commonly used tool for small RNA profiling and discovery in fields such as cancer, stem cell biology, and epigenetic gene regulation. Preparing samples for sRNA-seq requires construction of sequencing libraries (sRNA libraries). Difficulties arise when trying to analyze low frequency sequences due to the wide dynamic range of gene expression levels, which can vary by five orders of magnitude or more in a sample. Consequently, abundant RNA species can dominate sRNA libraries, requiring greater sequencing depth to obtain sufficient information for less abundant small RNAs present in the sample.

Current methods for reducing abundant RNAs are expensive, imprecise, add significant additional steps, and/or are not amenable to integration into current sRNA-seq protocols. One approach for depleting undesired RNA molecules from a sequencing library is based on hybridizing a complementary DNA or RNA oligonucleotide probe with an undesired RNA followed by removal of the probe-undesired RNA hybrid, typically utilizing a tag or marker on the probe, such as a biotin moiety. Another approach for depleting abundant RNA molecules prevents reverse transcription of abundant RNAs by hybridizing a "terminator" primer which cannot be extended. Another approach uses a double-stranded DNA nuclease (DSN) to deplete cDNAs representing abundant RNAs by denaturing dsDNA library molecules and allowing them to re-hybridize. Abundant cDNAs will re-hybridize more quickly than less abundant cDNAs and are thus more likely to be degraded by DSN, removing the high abundance cDNAs from the final sequencing library.

For at least the foregoing reasons, there is a need for methods and kits for depleting amplification products corresponding to one or more undesired RNA species from sRNA-seq libraries that are inexpensive, do not add significant additional steps, and/or can be integrated into existing sequencing library preparation and other nucleic acid amplification protocols.

SUMMARY

The current teachings disclose methods for depleting the number of amplification products corresponding to at least one undesired RNA species present in a sample. These methods are particularly useful in preparing sRNA-seq libraries. Kits suitable for performing certain disclosed methods are also provided.

Certain method embodiments for depleting at least one undesired RNA species comprise combining a sample with at least one blocker, at least one 3' adapter, and at least one first ligase to form a first reaction composition. The first reaction composition is incubated under conditions suitable for first ligation products to be formed. In various embodiments, the blocker is added before, simultaneously with, or after the 3' adapter. In various embodiments, the composition is incubated under conditions suitable for the blocker to anneal with the undesired RNA before, simultaneously with, or after the first ligation products are formed.

The first reaction composition comprising the first ligation products is combined with at least one 5' adapter and at least one second ligase to form a second reaction composition which is incubated under conditions suitable for second ligation products to be formed. The second reaction composition comprising the second ligation products is combined with suitable enzymes and the second ligation products are amplified to generate a pool of amplification products. The relative concentration of amplicons in the pool that correspond to the at least one undesired RNA species are depleted when compared to the relative concentration of that undesired RNA present in the sample. In certain embodiments, the pool of amplification products comprises a sRNA-seq library.

According to certain method embodiments for depleting at least one undesired RNA species, a sample is combined with at least one blocker, at least one 3' adapter, and at least one first ligase to form a first reaction composition and the first reaction composition is incubated under conditions suitable for first ligation products to form. In various embodiments, the blocker is added to the first reaction composition before, simultaneously with, or after the 3' adapter is added. In various embodiments, the first reaction composition is incubated under conditions suitable for the blocker to anneal with the corresponding undesired RNA before, simultaneously with, or after the first ligation products are formed. At least some of the first ligation products are separated from the first reaction composition and the separated first ligation products are combined with at least one 5' adapter and at least one second ligase to form a second reaction composition. The second reaction composition is incubated under conditions suitable for second ligation products to be formed and the second ligation products are amplified to generate a pool of amplification products. The amplification products corresponding to at least one undesired RNA species are depleted relative to that undesired RNA species present in the sample.

According to certain method embodiments for depleting at least one undesired RNA species, a sample comprising at least one undesired RNA species is combined with at least one 3' adapter, and at least one first ligase to form a first reaction composition and the composition is incubated under conditions suitable for first ligation products to be formed. The first reaction composition comprising the first ligation products is combined with at least one 5' adapter, at least one blocker, and at least one second ligase to form a second reaction composition and the second reaction composition is incubated under conditions suitable for second ligation products to be formed. According to various embodiments, the at least one blocker is added before, simultaneously with, or after the 5' adapter is added. In various embodiments, the second reaction composition is incubated under conditions suitable for the blocker to anneal with the undesired RNA or first ligation products comprising an undesired RNA before or simultaneously with the forming of the second ligation products. The second ligation products are amplified, generating a pool of amplification products. The concentration of amplification products corresponding to the at least one undesired RNA species in the pool of amplification products are depleted relative to the concentration of that undesired RNA species present in the sample.

According to certain method embodiments, a sample comprising at least one undesired RNA species is combined with at least one 3' adapter and at least one first ligase to form a first reaction composition and the composition is incubated under conditions suitable for first ligation products to be formed. At least some of the first ligation products are separated from the first reaction composition. The separated first ligation products are combined with at least one 5' adapter, at least one blocker, and at least one second ligase to form a second reaction composition. In various embodiments, at least one blocker is added before, simultaneously with, or after the 5' adapter is added. In various embodiments, the second reaction composition is incubated under conditions suitable for the blocker to anneal with the undesired RNA or first ligation products comprising undesired RNA either before or simultaneously with the forming of the second ligation products. The second ligation products are amplified to generate a pool of amplification products, wherein the amplification products corresponding to the at least one undesired RNA species are depleted.

Certain method and kit embodiments comprise: at least one blocker that is complementary to at least a portion of an undesired RNA species, wherein the complementary portion comprises a sequence that can anneal with at least the 5' end of the undesired RNA; at least one 3' adapter; and at least one 5' adapter. Certain methods and kits further comprise at least one T4 RNA ligase 2, at least one truncated T4 RNA ligase 2, at least one T4 RNA ligase 1, at least one *Methanobacterium thermoautotrophicum* RNA ligase, or combinations thereof. Certain method and kit embodiments comprise at least one species of 3' adapter comprising an activated adenylation (rApp) at its 5' end, a dideoxynucleotide (ddN) at its 3' end, or both an rApp at its 5' end and a ddN at its 3' end. According to certain method and kit embodiments, the ddN comprises ddC. According to certain method and kit embodiments, at least one blocker comprises at least one deoxyribonucleotide, at least one ribonucleotide, at least one locked nucleic acid (LNA), at least one 2' o-methyl nucleotide, at least one deoxyuridine, at least one inosine, or a combination thereof.

BRIEF DESCRIPTION OF THE FIGURES

These and other features and advantages of the current teachings will become better understood with regard to the following description, appended claims, and accompanying figures. The skilled artisan will understand that the figures, described below, are for illustration purposes only. The figures are not intended to limit the scope of the disclosed teachings in any way.

Figure 1:
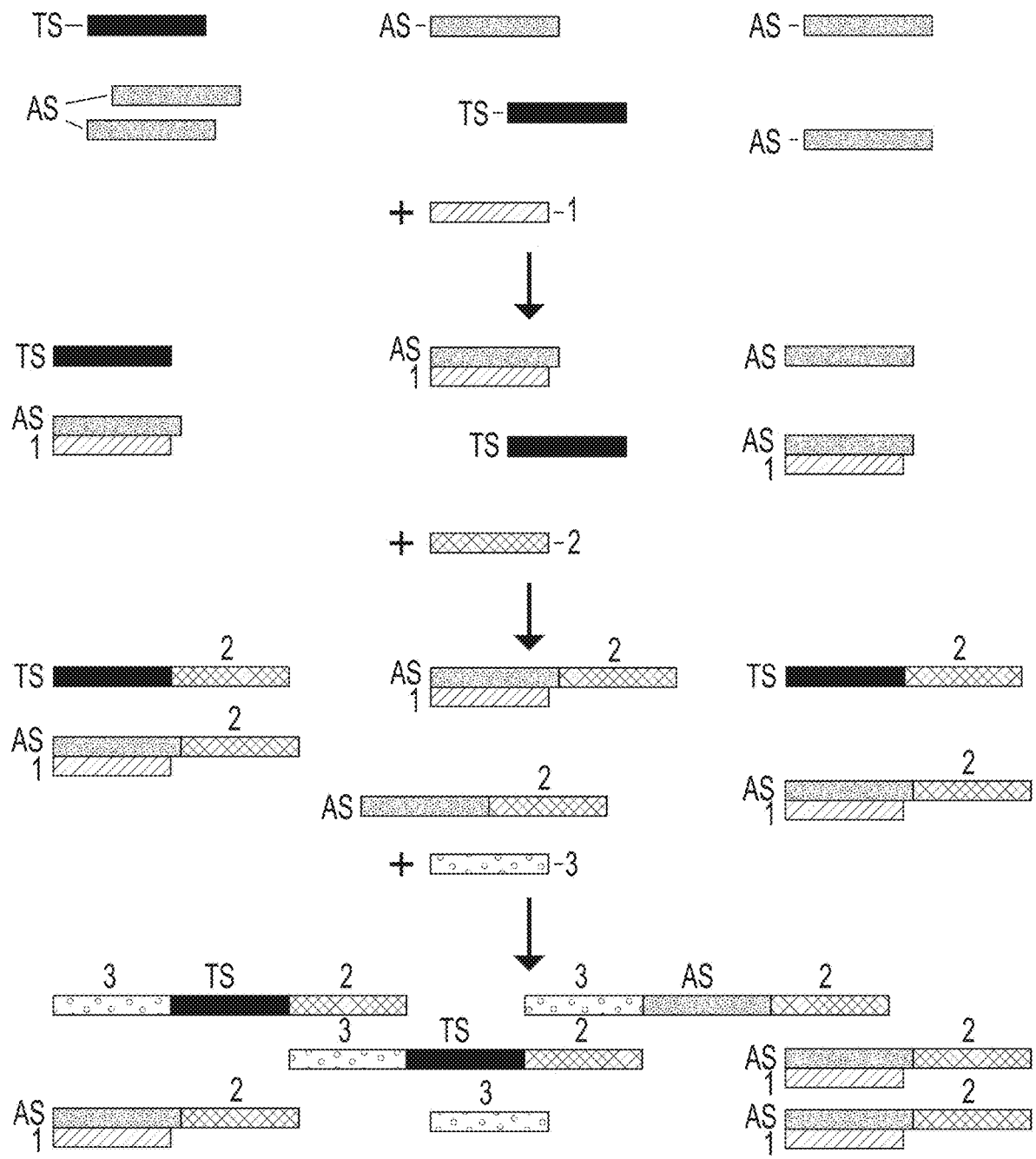
FIG. 1: schematically depicts a general overview of certain exemplary methods for depleting abundant or other undesired RNA species or their counterparts from a composition used for preparing sRNA-seq libraries.

DETAILED DESCRIPTION OF CERTAIN
EXEMPLARY EMBODIMENTS

It is to be understood that both the foregoing general description and the following detailed descriptions are illustrative and exemplary only and are not intended to limit the scope of the disclosed teachings. The section headings used herein are for organizational purposes only and are not to be construed as limiting the subject matter of the disclosed teachings.

In the Summary above, the Detailed Description, the accompanying figures, and the claims below, reference is made to particular features (including method steps) of the current teachings. It is to be understood that the disclosure in this specification includes possible combinations of such particular features. For example, where a particular feature is disclosed in the context of a particular embodiment of the current teachings, or a particular claim, that feature can also be used, to the extent possible, in combination with and/or in the context of other particular embodiments, and in the current teachings in general.

Where reference is made to a method comprising two or more combined steps, the defined steps can be performed in any order or simultaneously (except where the context excludes that possibility), and the method may also include one or more other steps which are carried out before any of the defined steps, between two of the defined steps, or after all of the defined steps (except where the context excludes that possibility).

Certain Definitions

The term "amplification product" as used herein refers to a single- or double-stranded nucleic acid that was generated using any nucleic acid amplification technique known in the art, for example, primer extension, the polymerase chain reaction (PCR), RNA transcription, and reverse transcription-polymerase chain reaction (RT-PCR). Thus, exemplary amplification products may comprise primer extension products, PCR amplicons, RNA transcription products, and so forth.

The term "blocker" as used herein, refers to an oligonucleotide that is complementary to or substantially complementary to at least a portion of an undesired RNA species. The blocker is designed to hybridize with sequences of the undesired RNA located at or near the 5' end of the undesired RNA species. In certain embodiments, the undesired RNA-blocker duplex comprises a "blunt end" on at least one end of the duplex (for example, the AS:1 duplex shown in FIG. 1). In certain embodiments, the end of the blocker extends beyond the end of the undesired nucleic acid to which it hybridizes. In certain embodiments, at least one blocker is a single-stranded DNA oligonucleotide or a single-stranded RNA oligonucleotide. In certain embodiments, at least one blocker comprises at least one deoxyribonucleotide and at least one ribonucleotide. Certain embodiments comprise a multiplicity of blocker species, each designed to anneal with at least a portion of an undesired RNA species, to allow depletion of multiple undesired RNA species. According to certain embodiments, at least one blocker comprises at least one nucleotide analog, for example, a dideoxynucleotide, a locked nucleic acid (LNA), a peptide nucleic acid (PNA), a 2'-O-methyl nucleotide, inosine, or deoxyuridine. In certain embodiments, the dideoxynucleotide comprises dideoxycytidine (ddC). The blocker is shorter, longer, or the same length as the undesired RNA to which it anneals.

The term "or combinations thereof" as used herein, refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth, if appropriate in the context in which the term is used.

As used herein, the term "comprising", which is synonymous with "including", and cognates of each (for example, comprises and includes), is inclusive or open-ended and does not exclude additional unrecited components, elements, or method steps, that is other components, steps, etc., are optionally present. For example, an article "comprising" components A, B, and C may consist of (that is, contain only) components A, B, and C; or the article may contain not only components A, B, and C, but also one or more additional components. Likewise, the term "for example" as used herein is intended to be open-ended, not limiting.

The term "depleting" as used herein refers to decreasing the relative number and/or the relative concentration of amplicons that correspond to one or more undesired RNA species in a pool of amplification products when compared to the number and/or concentration of copies of the corresponding to the undesired RNA species present in the sample. For illustration purposes, a sample may comprise undesired RNA species "X", with a copy number of 15,000 per cell or unit volume, and an RNA species of interest "Z", with a copy number of 250 per cell or unit volume. Following depletion of undesired RNA species X according to the current teachings, the pool of amplification products comprises 500 amplicons that correspond to undesired RNA species X and 50,000 amplicons corresponding to RNA species Z. Thus, (a) the sample in this illustration comprised 60 times as many copies of undesired RNA species X per unit volume than target RNA species Z per unit volume and (b) the pool of amplification products comprised 100 times more copies corresponding to RNA Z relative to those corresponding to undesired RNA species X; therefore, (c) undesired species X has been depleted relative to RNA species of interest Z. Likewise, exemplary undesired RNA species A may make up 10% of the RNA transcripts within a sample and RNA species B may make up 0.01% of the RNA species in the same sample. Following depletion of undesired RNA species A according to the disclosed methods and kits, amplification products corresponding to undesired RNA species A comprises 0.5% of the pool of amplification products, while the amplification products corresponding to RNA species B now represent 3% of the pool of amplification products.

The term "first ligation product" refers to the oligonucleotide that results from ligating a 3' adapter of the current teachings with an RNA that is present in the sample, schematically: RNA-3' adapter. The first ligation reaction, which results in the formation of first ligation products, is facilitated by a first ligase. The term "second ligation product" refers to the oligonucleotide that results from ligating a 5' adapter of the current teachings with a first ligation product, schematically: 5' adapter-RNA-3' adapter. The second ligation reaction, which results in the formation of second ligation products, is facilitated by a second ligase. In certain embodiments, the first ligase and the second ligase are the same.

"Primers" according to the current teachings refer to oligonucleotides that are designed to hybridize with a primer binding site on adapters, ligation products, or amplification products in a sequence-specific manner. When hybridized, primers facilitate at least some amplification reactions known in the art. In certain embodiments, a 3' adapter, a 5' adapter, or both a 3' adapter and a 5' adapter comprise a sequence that is the same as or is complementary to at least a portion of a primer.

The term "sample" is used in a broad sense and refers to any starting material that contains or may contain a nucleic acid sequence of interest. For example, a sample may comprise a cell lysate, a cellular extract, serum, blood, sputum, saliva, amniotic fluid, cerebral spinal fluid, urine, lymph, lavage fluid, synovial fluid, or other body fluid, purified or partially purified nucleic acid suspended in water or an appropriate buffer, a tissue or organ homogenate, biopsy material, a bone marrow or other cellular aspirate, or a subcellular fraction. The sample also contains or may contain at least one species of undesired RNA.

The term "separating first ligation products" is used in a broad sense herein and includes any technique known in the art for removing one or more components from a solution. In certain embodiments of the current teachings, at least some first ligation products are removed from the first reaction composition. In certain embodiments, at least some components of the first reaction composition comprising first ligation products are removed, leaving a residual composition comprising first ligation products, but at least substantially lacking one or more component of the first reaction composition. In either case, the separated first ligation products are combined with 5' adapters and a second ligase to form second reaction compositions. In certain embodiments, separated first ligation products are combined with blockers, 5' adapters, and a second ligase. Exemplary techniques for separating first ligation products comprise binding to and eluting from beads, for example Solid Phase Reversible Immobilization (SPRI) carboxylated magnetic beads (commercially available from Bioo Scientific), spin columns with filter membranes made of silica, and agarose or polyacrylamide gel electrophoresis.

The terms "undesired nucleic acid" and "undesired RNA" refer to an RNA molecule that may be, or is expected to be, present in the sample. In certain embodiments, the undesired RNA is a species that is present in high copy number in the sample, sometimes referred to as an abundant RNA species, for example, a transfer RNA species. In certain embodiments, an undesired RNA is a species that may not be present at high copy number in the sample, but is preferably depleted from the pool of amplification products generated from the starting material. Those of skill in the art will appreciate that it is the amplification product corresponding to the undesired RNA that is depleted according to the current teachings, rather than the undesired RNA species in the sample.

Certain Exemplary Reagents

Various embodiments of the disclosed methods and kits typically comprise at least one blocker, at least one first ligase, and at least one second ligase. In certain embodiments, a multiplicity of blocker species are used, wherein each blocker species is designed to anneal with a species of undesired RNA that may be present in the sample. In such embodiments, a multiplicity of undesired RNA species are depleted from the pool of amplification products generated according to the disclosed teachings.

Exemplary ligases include: T4 RNA ligase 1, *Methanobacterium thermoautotrophicum* thermostable RNA ligase, CIRCLIGASE™ RNA Ligase (Epicentre, Madison, Wis.), T4 RNA ligase 2 (including truncation mutants and point mutants thereof, such as AIR™ Ligase), Thermostable 5' AppDNA/RNA Ligase (New England Biolabs, Ipswich, Mass.), eukaryotic tRNA ligase, *E. coli* RNA ligase RtcB, and T4 DNA ligase. In certain embodiments, the first ligase comprises T4 RNA ligase 2 or truncated T4 RNA ligase 2 and at least one 3' adapter comprises an activated adenylation at its 5' end (5'rApp), a dideoxynucleotide (ddN) at its 3' end, or both a 5'rApp and a 3' ddN. In certain embodiments, the first ligase comprises T4 RNA ligase 1 and the first reaction composition further comprises ATP. In certain embodiments, the second ligase comprises T4 RNA ligase 1 or *Methanobacterium thermoautotrophicum* RNA ligase. In certain embodiments, the first ligase and the second ligase are the same, for example, two aliquots of T4 RNA ligase 1 added to separate steps or a thermostable ligase added to the first reaction composition. Those in the art will appreciate that a wide variety of prokaryotic and eukaryotic ligases, both thermo-labile and thermostable, as well as many viral ligases are suitable for use in the disclosed methods and kits. Virtually any ligase that effectively ligates a 3' adapter with an RNA molecule to form a first ligation product may be suitable for use as a first ligase according to the current teachings. Likewise, any ligase that effectively ligates a 5' adapter with a single-stranded first ligation product to form a second ligation product, but does not effectively ligate a 5' adapter with a first ligation product comprising a duplex, blunt end structure at its 5' end may be suitable for use as a second ligase according to the current teachings.

Certain Exemplary Methods

In certain embodiments, methods for depleting the relative amount of the amplification product corresponding to an undesired RNA species in a sample are provided. According to certain disclosed methods, a sample comprising at least one species of undesired RNA, at least one 3' adapter, and at least one first ligase are combined to form a first reaction composition. The first reaction composition is incubated under conditions suitable for at least some of the 3' adapters to be ligated to at least some RNA molecules to form first ligation products. Next, at least one 5' adapter and at least one second ligase are combined with the reaction composition comprising first ligation products to form a second reaction composition. The second reaction composition is incubated under conditions suitable for 5' adapters to be ligated to first ligation products to form second ligation products.

In various embodiments, the first reaction composition, the second reaction composition, or both the first and the second reaction compositions comprise at least one blocker species. In certain embodiments, a blocker is added before the 3' adapter, simultaneously with the 3' adapter, or after the 3' adapter is added. In certain embodiments, a first reaction composition comprising a blocker is incubated under conditions suitable for the blocker to anneal with the undesired RNA before, simultaneously with, or after the first ligation products are formed. In certain embodiments, a blocker is added to the first reaction composition comprising first ligation products before, simultaneously with, or after a 5' adapter is added to the composition.

Preferably, blockers anneal with at least the 5' end of a corresponding undesired RNA so that when annealed, a double-stranded duplex is formed at the 5' end of the undesired RNA. This duplex structure, which often comprises a "blunt" 5' end, is not an efficient ligation substrate. As a result, the number of possible second ligation products comprising that undesired RNA species are depleted. When the reaction composition comprising second ligation products is amplified, the relative concentration of amplification products corresponding to the undesired RNA species are depleted when compared to the relative concentration of that undesired RNA species in the sample, the concentration of amplification products corresponding to other RNA species in the sample, or both.

In certain embodiments, the second ligation products are amplified to yield a pool of amplification products wherein the amplification products corresponding to the undesired RNA are depleted relative to the copy number or concentration of that undesired RNA species in the sample. In certain embodiments, the amplifying comprises reverse transcription and polymerase chain reaction (RT-PCR). The skilled artisan will understand that various methods for amplifying nucleic acid known in the art may be suitable for use in the disclosed methods.

In certain embodiments, at least some amplification products are separated by size, for example by molecular weight, length, or mobility, prior to sequencing or other library analysis technique. Separating by molecular weight, length, or mobility according to the current teachings is used in the broad sense. Any method that allows a mixture of two or more nucleic acid sequences to be distinguished based on the mobility, molecular weight, or nucleotide length of a particular sequence is within the scope of the invention. Exemplary procedures for separating nucleic acids by size include electrophoresis, such as gel or capillary electrophoresis, HPLC, gel filtration, and mass spectroscopy including MALDI-TOF MS.

Certain Exemplary Kits

In certain embodiments, kits are provided to expedite the performance of various disclosed methods. Kits serve to expedite the performance of certain method embodiments by assembling two or more reagents and/or components used to performing one or more of the disclosed methods. Kits may contain reagents in pre-measured unit amounts to minimize the need for measurements by end-users. Kits may also include instructions for performing one or more of the disclosed methods. In certain embodiments, at least some of the kit components are optimized to perform in conjunction with each other. Typically, kit reagents may be provided in solid, liquid, or gel form.

Certain disclosed kit embodiments comprise at least one species of blocker, a 3' adapter, a 5' adapter, or combinations thereof. Certain kit embodiments further comprise at least one first ligase, at least one second ligase, or both a first ligase and a second ligase. Certain kit embodiments comprise at least one of: T4 RNA ligase 1, truncated T4 RNA ligase 2 (for example AIR™ Ligase, Bioo Scientific Corporation), T4 RNA ligase 2, and *Methanobacterium thermoautotrophicum* RNA ligase.

Certain Exemplary Embodiments

The current teachings are directed to methods and kits for generating pools of amplification products, for example a RNA sequencing library, from a sample comprising one or more undesired RNA species, wherein the amplification products that correspond to the one or more undesired RNA species present in a sample have been depleted in the pool of amplification products. For illustration purposes, an exemplary sample comprises 50,000 copies of undesired RNA species 1 per unit volume and 20 copies of target RNA species 2 per the same unit volume. Thus, the concentration of undesired RNA species 1 relative to the concentration of RNA species 2 in the sample is 2500:1. An RNA sequencing library, generated from this exemplary sample according to the current teachings, might comprise 1500 amplicons corresponding to undesired RNA species 1 and 15,000 amplicons corresponding to RNA species 2, each per unit volume. Therefore, in this illustration the concentration of undesired RNA species 1 relative to RNA species 2 was depleted from 2500:1 in the sample to 1:10 in the pool of amplification products.

According to various method embodiments, at least some undesired RNA molecules hybridize to blockers to form a duplex and thus will not be effectively ligated to a 5' adapter by the second ligase to form second ligation products. As the 5' adapter comprises a binding site for a primer, when the second ligation products are amplified using that primer, the number of amplicons corresponding to the undesired RNA species will be depleted relative to the concentration of that undesired RNA present in the sample. Consequently, amplification products corresponding to the undesired RNA species in the sample will be depleted and, as a result, will be at least under-represented in the pool of amplification products generated according to the disclosed methods and kits.

A general overview of certain exemplary embodiments is schematically depicted in FIG. 1. A sample comprising nucleic acids is obtained using methods known in the art. The sample comprises at least one RNA species of interest TS (also referred to as a target species) and at least one undesired RNA species AS. According to the disclosed methods and kits, the sequencing library generated from this sample retains at least some products that correspond to RNA species of interest while at least decreasing the relative number of amplification products that correspond to undesired RNA species. In certain embodiments, an undesired RNA species AS comprises an abundant RNA species that is present in the sample at high copy number relative to the target RNA species TS. In some embodiments, the undesired RNA species AS may not be present at high copy number relative to the target RNA species TS, but the presence of the amplification products corresponding to the undesired RNA species in the pool of amplification products may interfere with interpreting results or otherwise complicate downstream processing or analysis.

As shown in the top panel of FIG. 1, the sample is combined with at least one species of blocker 1 that is designed to hybridize with an undesired RNA species AS. The combination is incubated under conditions suitable for the blockers 1 to hybridize with complementary undesired RNA sequences AS to form duplexes, depicted as 1:AS duplexes. In various embodiments, at least one blocker is added before, simultaneously with, or after the 3' adapter and the undesired RNA species-blocker duplexes form before, simultaneously with, or after first ligation products are generated.

At least one 3' adapter 2 and at least one first ligase is added to form a first reaction composition (shown in FIG. 1, second panel from the top). The first reaction composition is incubated under conditions suitable for first ligation products to be generated, depicted schematically as AS-2 and TS-2 in the third panel of FIG. 1, where duplex AS-2 represents first ligation products comprising an undesired sequence AS ligated to 3' adapter 2; and oligonucleotide TS-2 represents first ligation products comprising a nucleic acid sequence of interest TS, or target sequence, ligated to 3' adapter 2. Also present in this reaction composition are oligonucleotide 1:AS duplex-3' adapter ligation products 1:AS-2, each comprising a double-stranded portion comprising an undesired RNA sequence AS hybridized with a blocker 1 to which a 3' adapter 2 has been ligated. At least one second ligase and at least one 5' adapter 3 is added to form a second reaction composition, as shown in the fourth (bottom) panel of FIG. 1. The second reaction composition is incubated under conditions suitable for second ligation products to be generated. As depicted in the bottom panel of FIG. 1, the second ligation products comprise a target RNA TS ligated to a 5' adapter 3 and a 5' adapter 2 (depicted as 3-TS-2) and an undesired RNA sequence AS ligated to a 5' adapter 3 and a 3' adapter 2 (depicted as 3-AS-2). In addition to second ligation products, this reaction composition contains at least some first reaction products, comprising undesired RNA species AS that are hybridized to blockers 1 that did not form second ligation products, depicted schematically as 1:AS-2 in the bottom panel of FIG. 1.

The second reaction composition comprising second ligation products is amplified, for example, using RT-PCR, to generate a pool of amplification products. The pool comprises at least some amplification products that correspond to target RNA sequences. The number of amplification products corresponding to those undesired RNA species has been depleted relative to the copy number of that undesired RNA species present in the sample. Thus, according to the disclosed methods and kits, the proportion of amplicons corresponding to those undesired RNA species represented in the sequencing library will be depleted relative to the corresponding proportion of those undesired RNA species present in the starting material. In certain embodiments, the starting material is total nucleic acid obtained from a tissue, cell, or organism. In some embodiments, the starting material comprises substantially DNA. In certain embodiments, the starting material comprises substantially RNA. In certain embodiments, the sample comprises small RNA, for example microRNA.

In certain embodiments, a total RNA preparation is suspended in nuclease-free water is used as the sample for preparing sRNA-libraries from which at least some undesired nucleic acid species have been depleted. A first reaction composition is formed comprising, the RNA sample, at least one single-stranded ("ss") DNA blocker, at least one ssRNA blocker, or both a ssDNA blocker and an ssRNA blocker, a ssDNA 3' adapter, a suitable buffer, and a first ligating enzyme, for example, truncated T4 RNA ligase 2. In certain embodiments, at least one 3' adapter comprises an activated adenylation (rApp) at its 5' end, a dideoxynucleotide or other blocking moiety at or near its 3' end, or both. The first reaction composition is incubated under conditions suitable for first ligation products to form.

In certain embodiments, at least some first ligation products in the first reaction composition are separated using techniques known in the art, for example, as embodied in certain clean-up kits such as the NEXTFLEX™ Small RNA Sequencing Kit v3 (Bioo Scientific), the NGS Library Cleanup Kit (MAGBIO), and the AGENCOURT® AMPure® XP kit (Beckman Coulter Life Sciences). In certain embodiments, residual excess 3' adapter is inactivated enzymatically, for example, according to the NEXTFLEX™ Small RNA Sequencing Kit v3 protocol.

In certain embodiments, ssRNA 5' adapters, ATP, and T4 RNA ligase 1, and optionally an appropriate buffer, are combined with the separated first ligation products to form a second reaction composition. The second reaction composition is incubated under conditions suitable for RNA ligation to occur, resulting in ligation of 5' adapter to the 5' end of the separated first ligation products.

The undesired RNA molecules that annealed with blockers to form blunt-ended double-stranded duplexes are a poor substrate for the second ligase, for example T4 RNA ligase 1, resulting in a significant reduction in the number of second ligation products comprising undesired RNA sequences. The second ligation products are amplified to form a pool of amplification products according to known methods, for example, various sRNA-seq library preparation protocols, for example, reverse transcription and PCR amplification. According to some embodiments, second ligation products or amplification products in a desired size range are selected using gel purification or other suitable size separation technique known in the art. For example, selecting the fraction of amplification products comprising microRNA sequences from the pool of amplification products using a size selection technique.

The skilled artisan will appreciate that a multiplicity of amplification products in the pool corresponding to undesired RNA species present in the sample may be depleted using for example, a multiplicity of different blocker species, wherein at least one species of blocker is designed to anneal with at least one of the multiple undesired RNA species initially present in the sample. It is to be understood that when multiple blocker species are employed according to the current teachings, multiple undesired RNA species may be depleted.

According to certain embodiments at least one blocker species is added during or subsequent to 3' adapter ligation, but prior to ligating the 5' adapter to first ligation products to form second ligation products.

Example 1. Construction of an exemplary sRNA-seq library. In an exemplary method embodiment, sRNA-seq libraries were prepared from human plasma total RNA. In a PCR plate, 4 nanograms (ng) total RNA was combined with water to a volume of 10.5 µL and heated to 70° C. for 2 minutes and then placed on ice. To each well of the PCR plate that contained the total RNA sample 1.25 picomoles pre-adenylated ssDNA 3' adapter 1 µL, 2 µL 10×AIR™ Ligase buffer (Bioo Scientific Corporation, Austin, Tex.), 5 µL 50% PEG (polyethylene glycol) 8000 and 1 AIR™ Ligase were added to form a first reaction composition in a total volume of 20 µL. The plate was incubated for 2 hours at 25° C. to allow 3' adapters to ligate onto the ends of target RNA molecules to form first ligation products. Following this incubation, 40 µL of NEXTFLEX™ cleanup beads, 25 µL of Adapter Depletion Solution (NEXTFLEX™ Small RNA Sequencing Kit v.3, Bioo Scientific) and 60 µL of isopropanol were added and the reaction mixed well and allowed to incubate at room temperature for 5 minutes. Next, the plate was placed on a magnetic rack and incubated for long enough to allow a bead pellet to form and the solution to clear. The supernatant was removed and discarded and the pellet washed twice with 80% ethanol by incubating with the ethanol for 30 seconds and then discarding the ethanol, without removing the plate from the magnetic rack. The bead pellet was allowed to dry by incubating at room temperature for 3 minutes, followed by removal of the plate from the magnetic stand and resuspension of the bead pellet with 22 µL of nuclease-free water. After incubating for two minutes at room temperature, the plate was placed on a magnetic rack to allow a bead pellet to form and the solution to clear. 20 of the cleared supernatant was transferred to another well of the PCR plate, and 40 µL of NEXTFLEX™ cleanup beads, 25 µL of Adapter Depletion Solution and 40 µL of isopropanol were added to each well with mixing and the plate was incubated at room temperature for 5 minutes. Next, the plate was placed on a magnetic rack and the beads were incubated for long enough for a bead pellet to form and the solution was clear. The supernatant was removed and discarded and the pellet washed twice with 80% ethanol by incubating with the ethanol for 30 seconds and then discarding the ethanol. The plate was not removed from the magnetic rack during these washes. The bead pellet was allowed to air dry at room temperature for 3 minutes, followed by removal of the plate from the magnetic stand and resuspension of the bead pellet with 13 µL of nuclease-free water. After incubating for two minutes at room temperature, the plate was placed on a magnetic rack for long enough for a bead pellet to form and the solution to clear. 11.5 µL of the cleared supernatant was transferred to another well, and 1.5 µL of Adapter Inactivation Reagent 1, 0.5 µL of Adapter Inactivation Reagent 2, and 0.5 µL of Adapter Inactivation Enzyme (NEXTFLEX™ Small RNA Sequencing Kit v.3, Bioo Scientific) added and the plate was incubated for 15 minutes at 12° C. followed by 20 minutes at 50° C. To each well of the plate containing first ligation products 0.625 picomoles ssRNA 5' adapter in a volume of 1.5 µL, 1.5 AIR™ ligase buffer, 4.5 µL PEG 8000, 15 nanomoles ATP, and T4 RNA ligase 1 were added in a total reaction volume of 25 µL. The plate was incubated for one hour at 22° C. to allow the 5' adapters to ligate to the first reaction products to form second ligation products. Reverse transcription was then performed to create cDNA from the second ligation products, and PCR was performed to generate a pool of amplification products for sRNA-seq.

Figure 2:
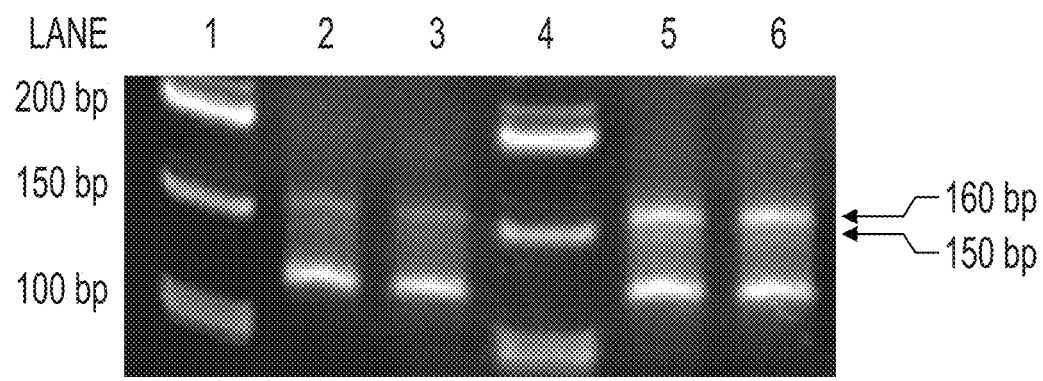
FIG. 2: depicts a polyacrylamide gel comprising an exemplary undesired sRNA-seq library product of approximately 160 base pairs (bp), corresponding to the amplification product of a known fragment of human YRNA, as described in Example 2. Lanes 1 and 4 comprise size markers; lanes 2 and 3 comprise sequencing libraries prepared from a first human plasma sample; lanes 5 and 6 comprise sequencing libraries prepared from a second human plasma sample.

Example 2. Amplification products corresponding to the undesired RNA species "YRNA" are present in sRNA-seq libraries prepared from human plasma. sRNA-seq libraries were prepared using 10-15 ng of human plasma total RNA according to the protocol of the NEXTFLEX™ Small RNA Sequencing Kit v3 (Bioo Scientific). A prominent band with a size of approximately 160 base pairs (bp) was observed in both samples in addition to a band of approximately 150 bp, characteristic of miRNAs (see FIG. 2, lanes 2, 3, 5, and 6). The relative intensity of the 160 bp and 150 bp bands varied between libraries. Material from the libraries depicted in lanes 2 and 4 of FIG. 2 were sequenced using an ILLUMINA® MiSeq® Sequencing System (Illumina, Inc., San Diego, Calif.). The resulting sequences revealed that most of the band observed at about 160 bp originated from a fragment of a YRNA transcript comprising the sequence: GGCUGGUCCGAUGGUAGUGGGUUAUCAGAACU (SEQ ID NO: 1).

Figure 3:
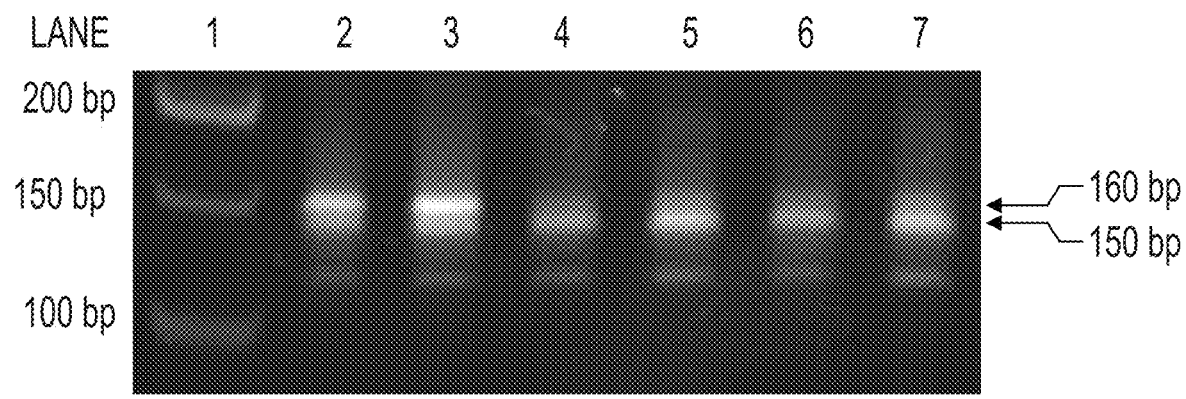
FIG. 3: depicts a polyacrylamide gel analysis of sequencing library products obtained according to an exemplary method of the current teachings, with and without a blocker that is designed to anneal with at least a portion of the YRNA fragment, as described in Example 3. Lane 1: Size marker; lanes 2 and 3: libraries prepared without YRNA blocker; lanes 4 and 5: libraries prepared using 10 picomole (@mole) of YRNA blocker; lanes 6 and 7: libraries prepared using 1 pmole of YRNA blocker, described in Example 3.

Example 3. Depletion of YRNA library products using an exemplary method of the current teachings. Six RNA sequencing libraries were prepared in parallel using 10-15 ng total RNA obtained from a human plasma, as described in Example 1, except that a DNA blocker with the sequence CCCACTACCATCGGACCAGCC (SEQ ID NO: 2) resuspended in water was added to aliquots of a first reaction composition to a final blocker concentration of either 0.1 or 1 µM before the initial heating. This blocker was designed to hybridize with the known YRNA fragment corresponding to the 160 bp amplicon described in Example 2. A control reaction comprising no blocker was also included. The resulting amplification products were analyzed by polyacrylamide gel electrophoresis, then stained with SYBR™ Gold (Thermo Fisher Scientific) according to known methods. A picture of the SYBR™ Gold stained gel comprising the resulting amplification products is shown in FIG. 3. Lanes 2 and 3 correspond to two reaction compositions that did not comprise the blocker. Lanes 4 and 5 of FIG. 3 correspond to libraries generated with 1.0 µM blocker and lanes 6 and 7 correspond to libraries generated with 0.1 µM blocker. Molecular size markers are shown in lane 1. All lanes corresponding to sequencing libraries generated with blocker (FIG. 3, lanes 4-7) show a significant reduction of the amplicons corresponding to the undesired YRNA amplification product (~160 bp) relative to the YRNA amplicons generated in library preparations not comprising the blocker (FIG. 3, lanes 2 and 3).

Figure 4A:
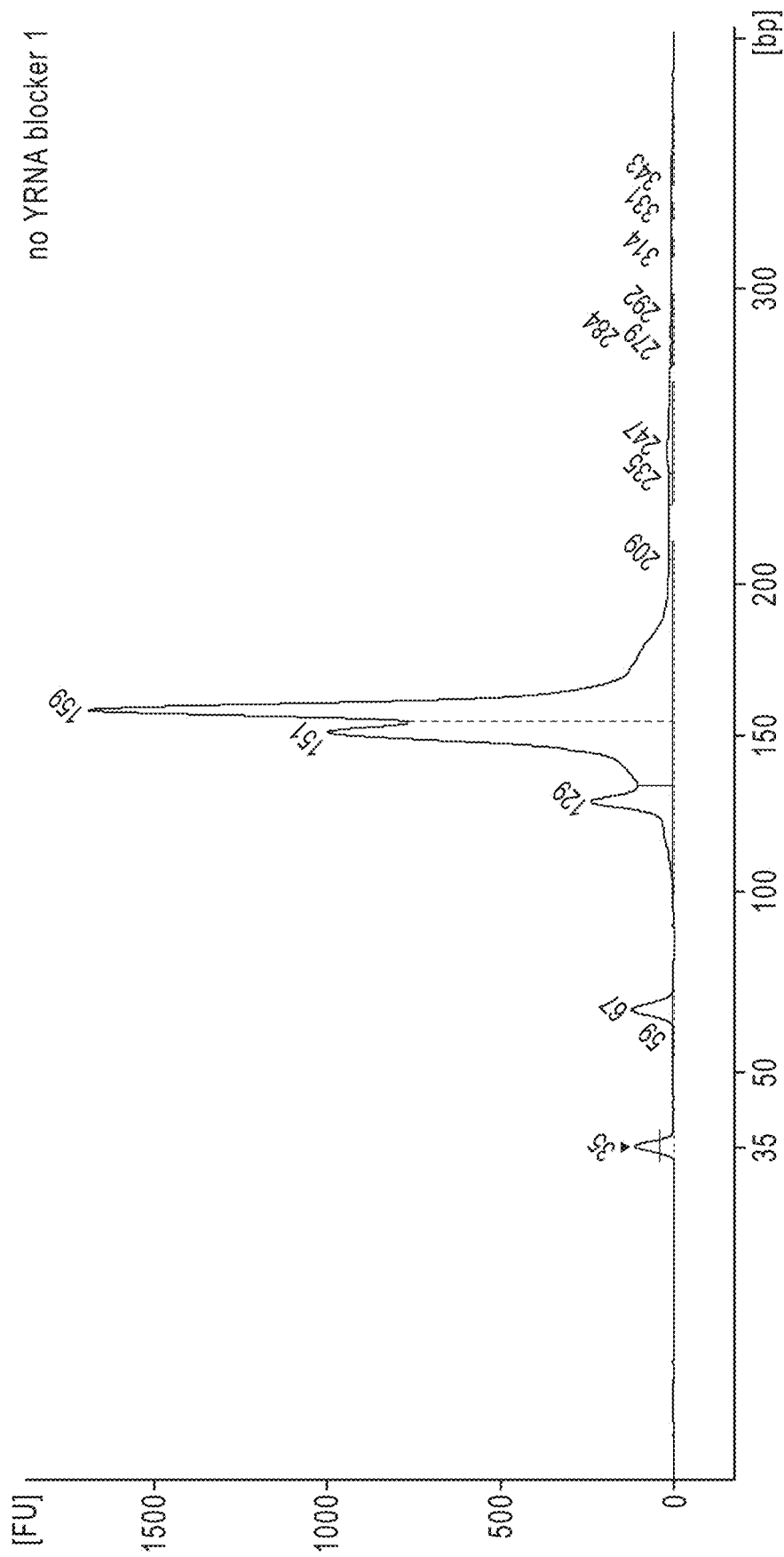
FIGS. 4A-C: graphically depicts the results obtained using an AGILENT® Bioanalyzer® High Sensitivity assay of amplicons present in sequencing libraries obtained according to an exemplary embodiment of the current teachings, as described in Example 4. The results shown in FIGS. 4A, 4B, and 4C correspond to sequencing libraries prepared in the absence of no blocker, 0.1 µM YRNA blocker, and 1.0 µM YRNA blocker, respectively.
Figure 4B:
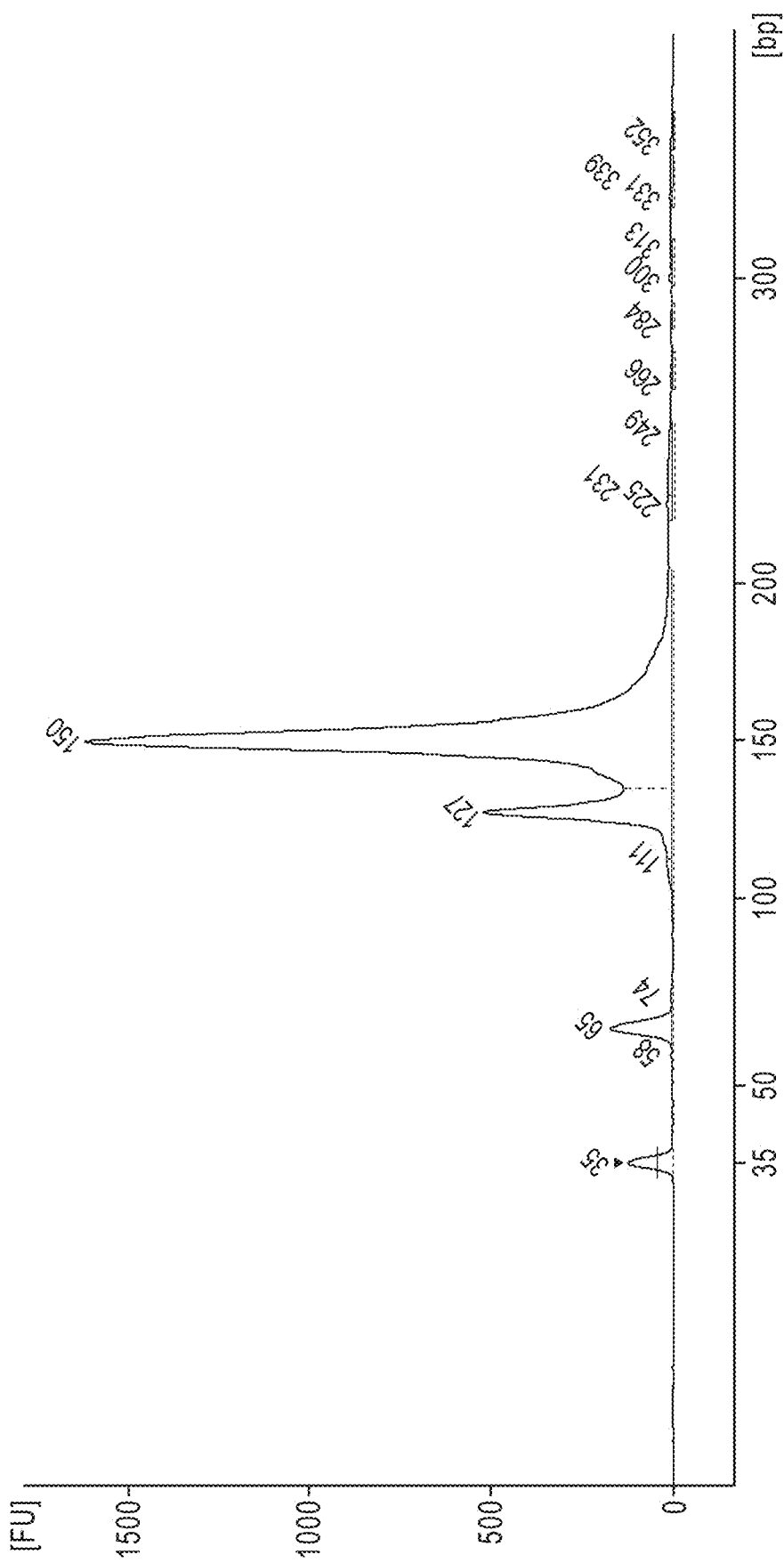
Figure 4C:
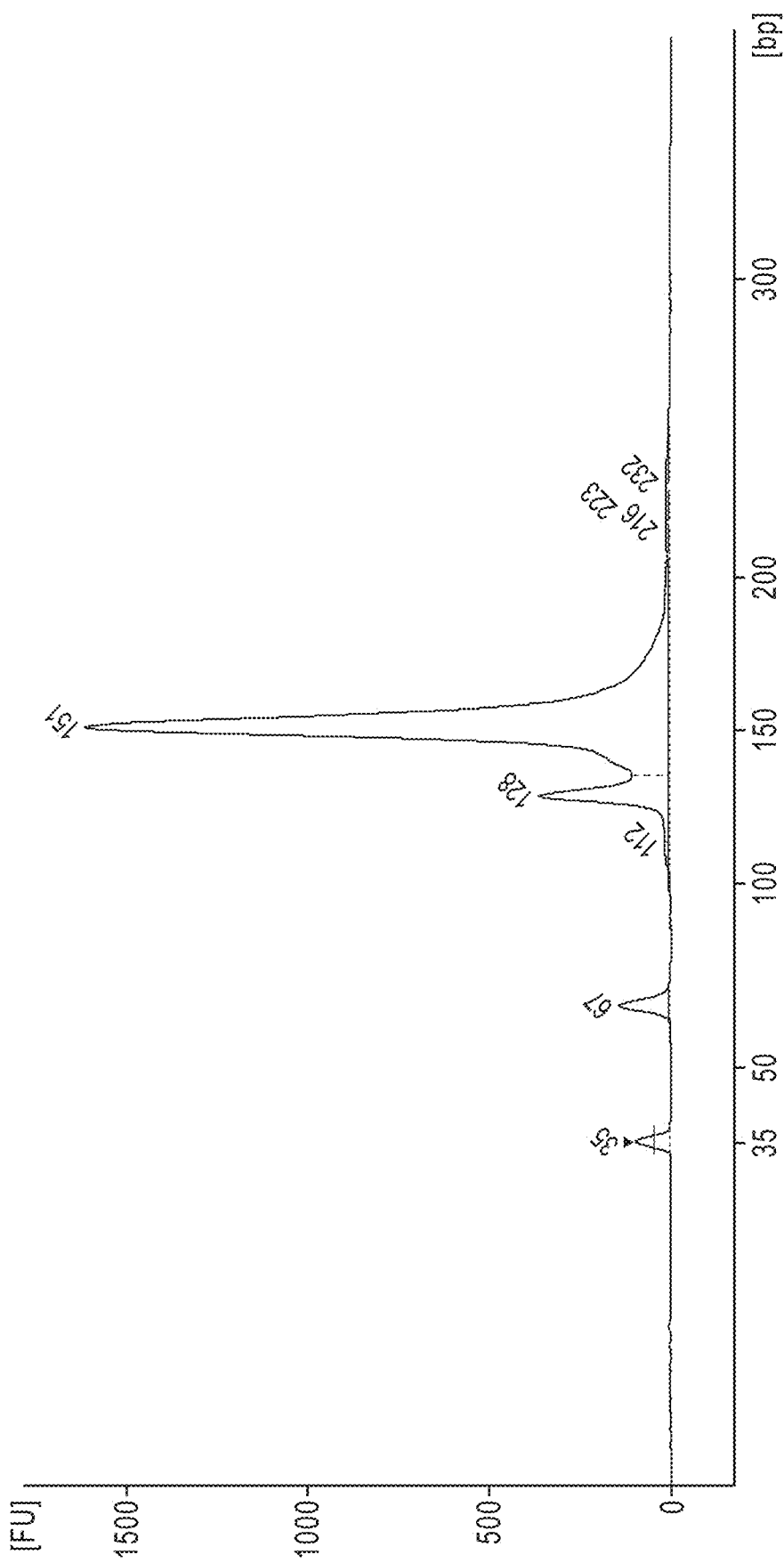

Example 4. Bioanalyzer® analysis of sequencing libraries prepared according to an exemplary embodiment. To further characterize the exemplary amplicon pools generated according to the exemplary method of Example 3, aliquots of the amplicon pools generated using no blocker (Example 3 prep 2), 1.0 µM blocker (Example 3prep 4), and 0.1 µM blocker (Example 3 prep 6) were analyzed using an Agilent® Bioanalyzer® 2100 (Agilent Technologies, Santa Clara, Calif.). As seen in FIG. 4A, the pool of amplification products generated without using the YRNA blocker contains a prominent peak at 159 bp, corresponding to the YRNA fragment amplification product and a lesser peak at 151 bp, corresponding to miRNA amplicons. When either 1.0 or 0.1 µM of the YRNA blocker were added in this exemplary method, the 160 bp peak corresponding to the YRNA fragment amplification product was not seen and the prominent peak is now at 150/151 bp, corresponding to miRNA amplicons (see FIG. 4B— 0.1 µM blocker; and FIG. 4C—1.0 µM YRNA blocker).

Figure 5:
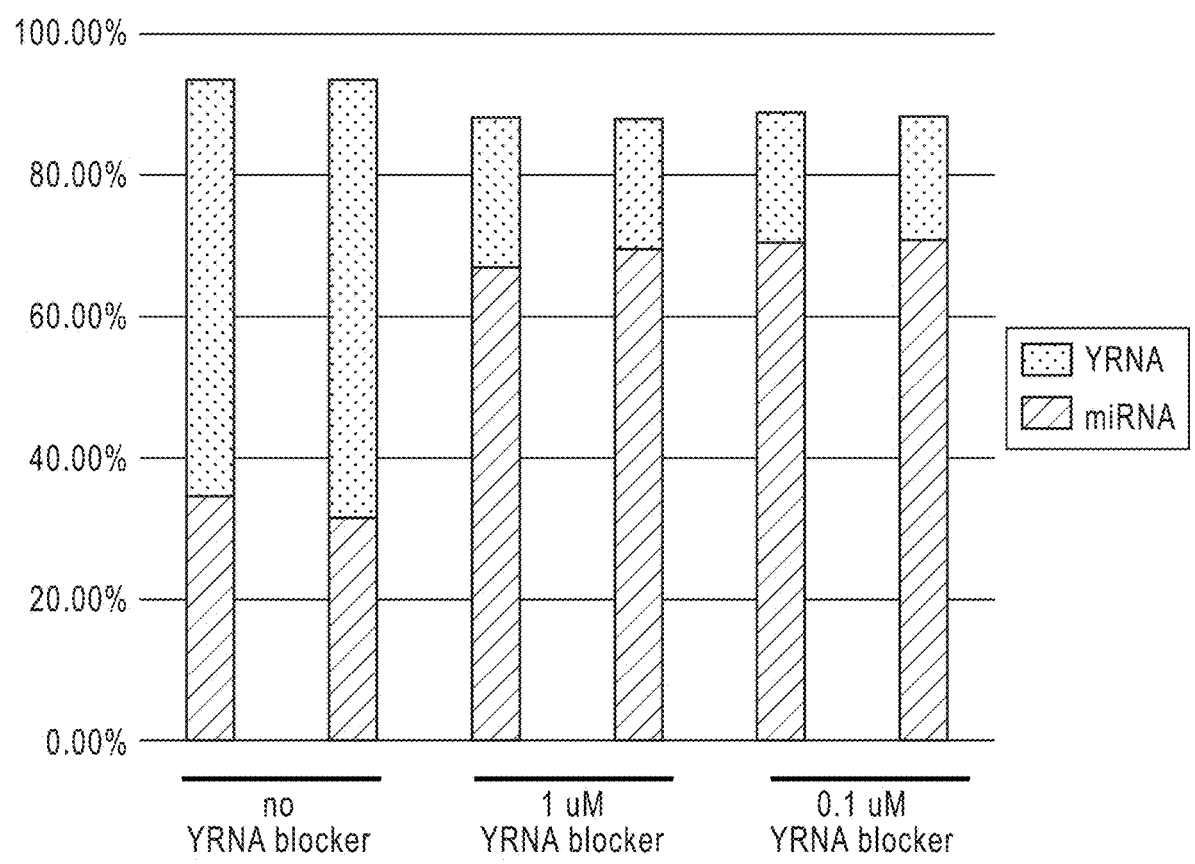
FIG. 5: depicts the percentage of sequences corresponding to undesired YRNA molecules (stippled portion of bar) detected compared to the percentage of sequences corresponding to miRNAs (diagonally striped portion of bar) detected in sRNA-seq libraries generated using an exemplary method, as described in Example 5.

Example 5. Sequencing analysis of exemplary libraries. To further evaluate whether the disclosed methods result in depletion of undesired RNA species, the libraries generated in Example 3 were sequenced on an ILLUMINA® MiSeq® Sequencing System (Illumina, San Diego, Calif.). As depicted in FIG. 5, libraries generated without a blocker contain less than 40% of the sequencing reads correspond to a miRNA (cross-hatched bars), while over 50% the sequencing reads correspond to the undesired YRNA fragment (stippled bars). In contrast, when aliquots of the amplification pools generated using either 1.0 or 0.1 µM YRNA blocker were sequenced, approximately 70% of the sequencing reads correspond to a miRNA with approximately 15% of the sequencing reads corresponding to the undesired YRNA fragment.

Example 6. Depletion of miRNA-486, an Undesired microRNA Present in Whole Blood miR-486 is an extremely abundant miRNA in human whole blood, often representing 50% or more of all sequencing reads in a small RNA sequencing library. Thus, reduction of reads representing miR-486 would be useful for investigators creating small RNA sequencing libraries from whole blood RNA.

To deplete miR-486 according to the current teachings, a blocker comprising the sequence CTCGGGGCAGCTCAGTACAGGA (SEQ ID NO: 3), the reverse complement of the miR-486 sequence, is employed. According to certain disclosed methods, the blocker is annealed to miR-486 to form a blocker:miR-486 duplex. Because the blocker:miR-486 duplex is not efficiently ligated to 5' adapters, the number of second ligation products comprising the miR-486 sequence or its complement will be decreased. Consequently, the proportion of reads mapping to miR-486 in sequencing libraries prepared from human whole blood RNA samples will be depleted, allowing lower copy number RNA sequences in the sample to be more readily detected and quantitated in the pool of amplification products.

Although the disclosed teachings have been described with reference to various applications, methods, and compositions, it will be appreciated that various changes and modifications may be made without departing from the teachings herein. The foregoing examples are provided to better illustrate the present teachings and are not intended to limit the scope of the teachings herein. Furthermore, various presently unforeseen or unanticipated alternatives, modifications, variations or improvements therein may be subsequently made by those skilled in the art which are also intended to be encompassed by the following claims. Certain aspects of the present teachings may be further understood in light of the following claims.

What is claimed is:

1. A method for depleting at least one undesired RNA species having a 5' end of the undesired RNA and a 3' end of the undesired RNA, comprising:

combining a sample with at least one single-stranded nucleic acid blocker having a 5' end of the blocker and a 3' end of the blocker, at least one 3' adapter, and at least one first ligase to form a first reaction composition and incubating under conditions suitable for first ligation products to be formed, wherein the single-stranded nucleic acid blocker is added before, simultaneously with, or after the 3' adapter, and wherein the first reaction composition is incubated under conditions suitable for the single-stranded nucleic acid blocker to anneal with the undesired RNA to form an RNA-blocker duplex, wherein the RNA-blocker duplex has a blunt duplex end comprising the 5' end of the undesired RNA and the 3' end of the blocker, or wherein the 3' end of the blocker extends beyond the 5' end of the undesired RNA in the RNA-blocker duplex, such that the 3' end of the blocker is not present in the RNA-blocker duplex, wherein the RNA-blocker duplex is formed before, simultaneously with, or after the first ligation products are formed, and wherein the blocker does not form a unimolecular duplex under the conditions suitable for the single-stranded nucleic acid blocker to anneal with the undesired RNA to form an RNA-blocker duplex;

combining the first reaction composition comprising the first ligation products with at least one 5' adapter and at least one second ligase to form a second reaction composition and incubating under conditions suitable for second ligation products to be formed;

wherein neither the 5' end of the blocker nor the 3' end of the blocker is ligated to the undesired RNA; and amplifying the second ligation products to generate a pool of amplification products, wherein amplification products corresponding to the at least one undesired RNA species are depleted.

2. The method of claim 1, wherein the amplifying comprises reverse transcription-polymerase chain reaction (RT-PCR).

3. The method of claim 1, wherein the first ligase comprises T4 RNA ligase 2 or truncated T4 RNA ligase 2 and the second ligase comprises T4 RNA ligase 1 or *Methanobacterium thermoautotrophicum* RNA ligase.

4. The method of claim 1, wherein the first ligase comprises T4 RNA ligase 1, and wherein the first reaction further comprises ATP.

5. The method of claim 1, wherein the single-stranded nucleic acid blocker comprises at least one deoxyribonucleotide, at least one ribonucleotide, at least one locked nucleic acid (LNA), at least one 2'-O-methyl nucleotide, at least one deoxyuridine, at least one inosine, or combinations thereof.

6. The method of claim 1, wherein the single-stranded nucleic acid blocker is shorter or the same length as the undesired RNA to which it anneals.

7. The method of claim 1, wherein the sample comprises at least one small RNA species.

8. The method of claim 1, wherein the amplifying comprises adding at least one oligonucleotide primer and at least one reverse transcriptase to the second ligation products to generate double-stranded second ligation products.

9. The method of claim 1, further comprising separating at least some of the amplification products by size.

10. The method of claim 1, wherein at least one 3' adapter comprises an activated adenylation (rApp) at its 5' end, a dideoxy nucleotide at its 3' end, or an rApp at its 5' end and a dideoxy nucleotide at its 3' end.

11. A method for depleting at least one undesired RNA species having a 5' end of the undesired RNA and a 3' end of the undesired RNA, comprising:
combining a sample with at least one single-stranded nucleic acid blocker having a 5' end of the blocker and a 3' end of the blocker, at least one 3' adapter, and at least one first ligase to form a first reaction composition and incubating under conditions suitable for first ligation products to be formed, wherein the single-stranded nucleic acid blocker is added before, simultaneously with, or after the 3' adapter, and wherein the first reaction composition is incubated under conditions suitable for the single-stranded nucleic acid blocker to anneal with the undesired RNA to form an RNA-blocker duplex, wherein the RNA-blocker duplex has a blunt duplex end comprising the 5' end of the undesired RNA and the 3' end of the blocker, or wherein the blocker extends beyond the 5' end of the undesired RNA in the RNA-blocker duplex, wherein the RNA-blocker duplex is formed before, simultaneously with, or after the first ligation products are formed, and wherein the blocker does not form a unimolecular duplex under the conditions suitable for the single-stranded nucleic acid blocker to anneal with the undesired RNA to form an RNA-blocker duplex;
separating the first ligation products from the first reaction composition;
combining the separated first ligation products with at least one 5' adapter and at least one second ligase to form a second reaction composition and incubating under conditions suitable for second ligation products to be formed;
wherein neither the 5' end of the blocker nor the 3' end of the blocker is ligated to the undesired RNA; and
amplifying the second ligation products to generate a pool of amplification products, wherein amplification products corresponding to the at least one undesired RNA species are depleted.

12. The method of claim 11, wherein the amplifying comprises RT-PCR.

13. The method of claim 11, wherein the first ligase comprises T4 RNA ligase 2 or truncated T4 RNA ligase 2 and the second ligase comprises T4 RNA ligase 1 or *Methanobacterium thermoautotrophicum* RNA ligase.

14. The method of claim 11, wherein the first ligase comprises T4 RNA ligase 1, and wherein the first reaction further comprises ATP.

15. The method of claim 11, wherein the single-stranded nucleic acid blocker comprises at least one deoxyribonucleotide, at least one ribonucleotide, at least one LNA, at least one 2'-O-methyl nucleotide, at least one deoxyuridine, at least one inosine, or combinations thereof.

16. The method of claim 11, wherein the single-stranded nucleic acid blocker is shorter or the same length as the undesired RNA to which it anneals.

17. The method of claim 11, wherein the sample comprises at least one small RNA species.

18. The method of claim 11, wherein the amplifying comprises adding at least one oligonucleotide primer and at least one reverse transcriptase to the second ligation products to generate double-stranded second ligation products.

19. The method of claim 11, further comprising separating at least some of the amplification products by size.

20. The method of claim 11, wherein at least one 3' adapter comprises an rApp at its 5' end, a dideoxy nucleotide at its 3' end, or an rApp at its 5' end and a dideoxy nucleotide at its 3' end.

21. A method for depleting at least one undesired RNA species having a 5' end of the undesired RNA and a 3' end of the undesired RNA, comprising:
combining a sample with at least one 3' adapter and at least one first ligase to form a first reaction composition and incubating under conditions suitable for first ligation products to be formed;
combining the first reaction composition comprising the first ligation products with at least one 5' adapter, at least one single-stranded nucleic acid blocker having a 5' end of the blocker and a 3' end of the blocker, and at least one second ligase to form a second reaction composition and incubating under conditions suitable for second ligation products to be formed, wherein the at least one single-stranded nucleic acid blocker is added before, simultaneously with, or after the 5' adapter, and wherein the second reaction composition is incubated under conditions suitable for the single-stranded nucleic acid blocker to anneal with the undesired RNA or first ligation products comprising undesired RNA to form an RNA-blocker duplex, wherein the RNA-blocker duplex has a blunt duplex end comprising the 5' end of the undesired RNA and the 3' end of the blocker, or wherein the blocker extends, in single-stranded form, beyond the 5' end of the undesired RNA in the RNA-blocker duplex, wherein the RNA-blocker duplex is formed before or simultaneously with the forming of the second ligation products; and
amplifying the second ligation products to generate a pool of amplification products, wherein amplification products corresponding to the at least one undesired RNA species are depleted.

22. The method of claim 21, wherein the amplifying comprises RT-PCR.

23. The method of claim 21, wherein the first ligase comprises T4 RNA ligase 2 or truncated T4 RNA ligase 2 and the second ligase comprises T4 RNA ligase 1 or *Methanobacterium thermoautotrophicum* RNA ligase.

24. The method of claim 21, wherein the first ligase comprises T4 RNA ligase 1, and wherein the first reaction further comprises ATP.

25. The method of claim 21, wherein the single-stranded nucleic acid blocker comprises at least one deoxyribonucleotide, at least one ribonucleotide, at least one LNA, at least one 2'-O-methyl nucleotide, at least one deoxyuridine, at least one inosine, or combinations thereof.

26. The method of claim 21, wherein the single-stranded nucleic acid blocker is shorter or the same length as the undesired RNA to which it anneals.

27. The method of claim 21, wherein the sample comprises at least one small RNA species.

28. The method of claim 21, wherein the amplifying comprises adding at least one oligonucleotide primer and at least one reverse transcriptase to the second ligation products to generate double-stranded second ligation products.

29. The method of claim 21, further comprising separating at least some of the amplification products by size.

30. The method of claim 21, wherein at least one 3' adapter comprises an rApp at its 5' end, a dideoxy nucleotide at its 3' end, or an rApp at its 5' end and a dideoxy nucleotide at its 3' end.

31. A method for depleting at least one undesired RNA species having a 5' end of the undesired RNA and a 3' end of the undesired RNA, comprising:
  combining a sample with at least one 3' adapter and at least one first ligase to form a first reaction composition and incubating under conditions suitable for first ligation products to be formed;
  separating the first ligation products from the first reaction composition;
  combining the separated first ligation products with at least one 5' adapter, at least one single-stranded nucleic acid blocker having a 5' end of the blocker and a 3' end of the blocker, and at least one second ligase to form a second reaction composition and incubating under conditions suitable for second ligation products to be formed, wherein the at least one single-stranded nucleic acid blocker is added before, simultaneously with, or after the 5' adapter, and wherein the second reaction composition is incubated under conditions suitable for the single-stranded nucleic acid blocker to anneal with the undesired RNA or first ligation products comprising undesired RNA to form an RNA-blocker duplex, wherein the RNA-blocker duplex has a blunt duplex end comprising the 5" end of the undesired RNA and the 3' end of the blocker, or wherein the blocker extends, in single-stranded form, beyond the 5' end of the undesired RNA in the RNA-blocker duplex, wherein the RNA-blocker duplex is formed before or simultaneously with the forming of the second ligation products; and
  amplifying the second ligation products to generate a pool of amplification products, wherein amplification products corresponding to the at least one undesired RNA species are depleted.

32. The method of claim 31, wherein the amplifying comprises RT-PCR.

33. The method of claim 31, wherein the first ligase comprises T4 RNA ligase 2 or truncated T4 RNA ligase 2 and the second ligase comprises T4 RNA ligase 1 or *Methanobacterium* thermoautotrophicum RNA ligase.

34. The method of claim 31, wherein the first ligase comprises T4 RNA ligase 1, and wherein the first reaction further comprises ATP.

35. The method of claim 31, wherein the single-stranded nucleic acid blocker comprises at least one deoxyribonucleotide, at least one ribonucleotide, at least one LNA, at least one 2'-O-methyl nucleotide, at least one deoxyuridine, at least one inosine, or combinations thereof.

36. The method of claim 31, wherein the single-stranded nucleic acid blocker is shorter or the same length as the undesired RNA to which it anneals.

37. The method of claim 31, wherein the sample comprises at least one small RNA species.

38. The method of claim 31, wherein the amplifying comprises adding at least one oligonucleotide primer and at least one reverse transcriptase to the second ligation products to generate double-stranded second ligation products.

39. The method of claim 31, further comprising separating at least some of the amplification products by size.

40. The method of claim 31, wherein at least one 3' adapter comprises an rApp at its 5' end, a dideoxy nucleotide at its 3' end, or rApp at its 5' end and a dideoxy nucleotide at its 3' end.

* * * * *

SEQUENCE LISTING

<160> NUMBER OF SEQ ID NOS: 3

<210> SEQ ID NO 1
<211> LENGTH: 32
<212> TYPE: RNA
<213> ORGANISM: Homo sapiens

<400> SEQUENCE: 1
ggcugguccg augguagugg guuaucagaa cu                                      32

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 2
cccactacca tcggaccagc c                                                  21

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 3
ctcggggcag ctcagtacag ga                                                 22